United States Patent [19]
Brefka

[11] 3,932,263
[45] Jan. 13, 1976

[54] ELECTROPHORESIS SLIDE MOUNTING MEANS

[75] Inventor: Paul E. Brefka, Southborough, Mass.

[73] Assignee: Millipore Corporation, Bedford, Mass.

[22] Filed: Nov. 4, 1974

[21] Appl. No.: 520,286

[52] U.S. Cl. .......... 204/299; 204/180 S; 204/180 G
[51] Int. Cl.² .......................................... B01K 5/00
[58] Field of Search ............ 204/299, 180 G, 180 S

[56] References Cited
UNITED STATES PATENTS

| | | |
|---|---|---|
| 3,317,417 | 5/1967 | Raymond ............................ 204/299 |
| 3,421,998 | 1/1969 | Yallen ................................. 204/299 |
| 3,594,263 | 7/1971 | Dwyer et al. ................. 204/180 S X |
| 3,666,655 | 5/1972 | Nybom .............................. 204/299 |
| 3,798,152 | 3/1974 | Cawley ............................. 204/299 |

Primary Examiner—John H. Mack
Assistant Examiner—A. C. Prescott
Attorney, Agent, or Firm—Kenway & Jenney

[57] ABSTRACT

Apparatus for holding an electrophoresis slide of agarose gel against the concave surface of a slide mounting block is described. The holding means permits the slide to be inserted readily and holds the slide in compression in intimate contact with the concave surface.

3 Claims, 2 Drawing Figures

ELECTROPHORESIS SLIDE MOUNTING MEANS

BACKGROUND OF THE INVENTION

Electrophoresis is a method for the analysis of proteins in body fluids and has proven to be very valuable in laboratory and clinical work. There have been a number of commercial instruments produced for relatively low resolution applications, in which the electrophoretic medium is a microporous plastic membrane or a polyacrylamide gel which permits resolution of perhaps five components in the material being analyzed. Much higher resolution and accordingly analysis of as many as fifteen components may be obtained utilizing a relatively large area of agarose gel slide which is subjected to electrophoresis under specified controlled condition. Such a slide is formed of an agarose gel with a barbital buffer added. While measurements performed with these slides have shown excellent results in laboratory environments, in order to attain wide spread clinical use, an apparatus for providing easy, economical and particularly accurate and reproducible results is required.

In electrophoresis, the initial step is to apply the sample material to the electrophoretic medium and allow the separation to take place by migration under the influence of an applied electric field. Thereafter the slide is fixed chemically, dried and subsequently read either directly or with appropriate densitometer devices. To obtain a practical migration apparatus, the device must be capable of obtaining accurate and highly reproducible results even when operated by relatively unskilled technicians. In order to provide such accuracy and reproducibility, there are a number of variables which must be precisely controlled. These include the value of the applied voltage, the time duration for migration, the voltages applied, the geometry of mounting and holding the slide during the period of migration and the temperature maintained during the period of migration.

For a large area of slide, for example, a rectangular slide approximately 9 by 6 inches, with an applied voltage of approximately 200 volts, the slide would undergo an increase in temperature to values above 55°C. At these elevated temperatures, drying of the slide occurs with an increase in ionic concentration, in turn causing further power dissipation and further increase in temperature. Additionally, denaturing of proteins takes place at these high temperatures. Finally, it is desirable to maintain the slide in a constant temperature environment during electrophoresis. Variations in slide temperature during separation, while not affecting information content, do cause variations in mobility of individual protein components during electrophoresis. By performing electrophoretic separation at a constant temperature comparison of patterns between slides is facilitated.

In the past, various conventional cooling techniques have been employed. These include both water cooling a member in thermal contact with the slide and various air cooling approaches. For a slide which must necessarily have each of its ends inserted in a chemically active buffer material and have a voltage of approximately 200 volts applied across it, such cooling arrangements complicate the design of the migration apparatus and render it somewhat difficult to manipulate in routine laboratory procedures.

It is, therefore, the primary object of the present invention to provide an electrophoresis migration apparatus allowing for ease of handling, economy of operation, and precise results, while maintaining the electrophoretic slide at a substantially constant temperature between 5°C and 40°C.

SUMMARY OF THE INVENTION

Broadly speaking, in the present invention, a rectangular electrophoresis slide is mounted with the substrate portion of the slide in intimate contact with an external concave cylindrical surface of the mounting block. The interior of the block contains salts, which melt at a temperature a few degrees above room temperature as for example about 29°C. The heat required to liquefy the salt is removed from the surface which is in contact with the slide. This concave surface is formed of a material which is electrically insulating, hydrophobic, and does not interact chemically with the buffer material. The mounting block is configured to be positioned in a sealed relationship with a buffer reservoir divided into two isolated buffer cells, each containing the appropriate barbituate buffer solution, and each having an opposite polarity electrode in contact with the solution. A power supply for providing appropriate voltage at sufficient power levels is connected between the two electrodes. The slide mounting block is arranged to provide for positive retention of the slide compressed sufficiently to ensure continuous intimate contact between the substrate of the slide and the concave surface of the mounting block. With the slide so positioned, when the mounting block is placed over the reservoir, the ends of the slide are located within the buffer solution and, when the voltage is applied, the electrophoretic migration takes place.

In order to facilitate quick, accurate and positive mounting of the agarose gel electrophoresis slide, a specific means for mounting and retaining the slide in contact with the concave surface of the coating block is provided. The means comprises a flat generally rectangular strip of highly resilient soft material, such as closed cell foam rubber or silicon elastomer positioned to extend generally normal to the concave surface. The opposite end of the concave surface is fitted with a rigid rectangular retaining element similarly oriented. The problem encountered in mounting and retaining the silicon slide is that one surface of it is coated with the agarose gel which must be maintained uncontaminated and yet it is important that the undeside of the substrate, typically polyethylene film, be maintained in close, substantially continuous contact with the concave surface in order to provide uniformity of cooling across the film. Thus, some compression force is required both in mounting and in retaining the slide and both must be applied bearing in mind the general delicacy of the slide itself.

In operation, the slide is gripped by the nongel borders and one end is placed in contact with the concave surface and slid until that end is pressing against the soft resilient member. The entire slide is then pushed into close contact and the free end is snapped under the rigid retaining element at the opposite end of the concave surface. The resiliency of the compressible lip retaining member now maintains the entire slide in compression against the curved surface.

THE DRAWINGS

In the drawing:

FIG. 1 is an illustration generally in perspective view of a mounting block and buffer reservoir assembly constructed in accordance with the principles of this invention; and FIG. 2 is an illustration in cross sectional view taken along the lines 2-2 of FIG. 1.

DESCRIPTION OF PREFERRED EMBODIMENTS

Figure 1:
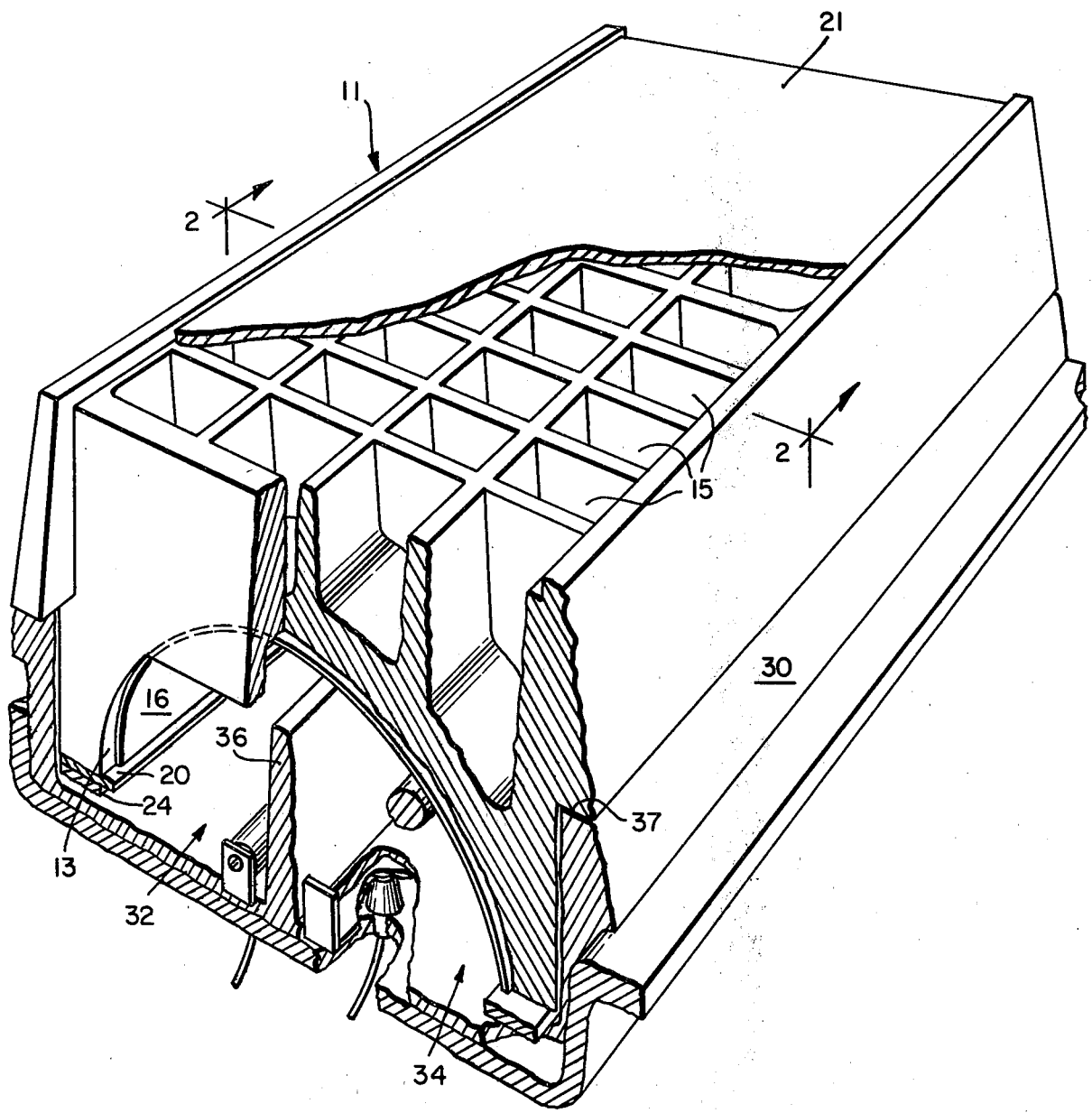
Figure 2:
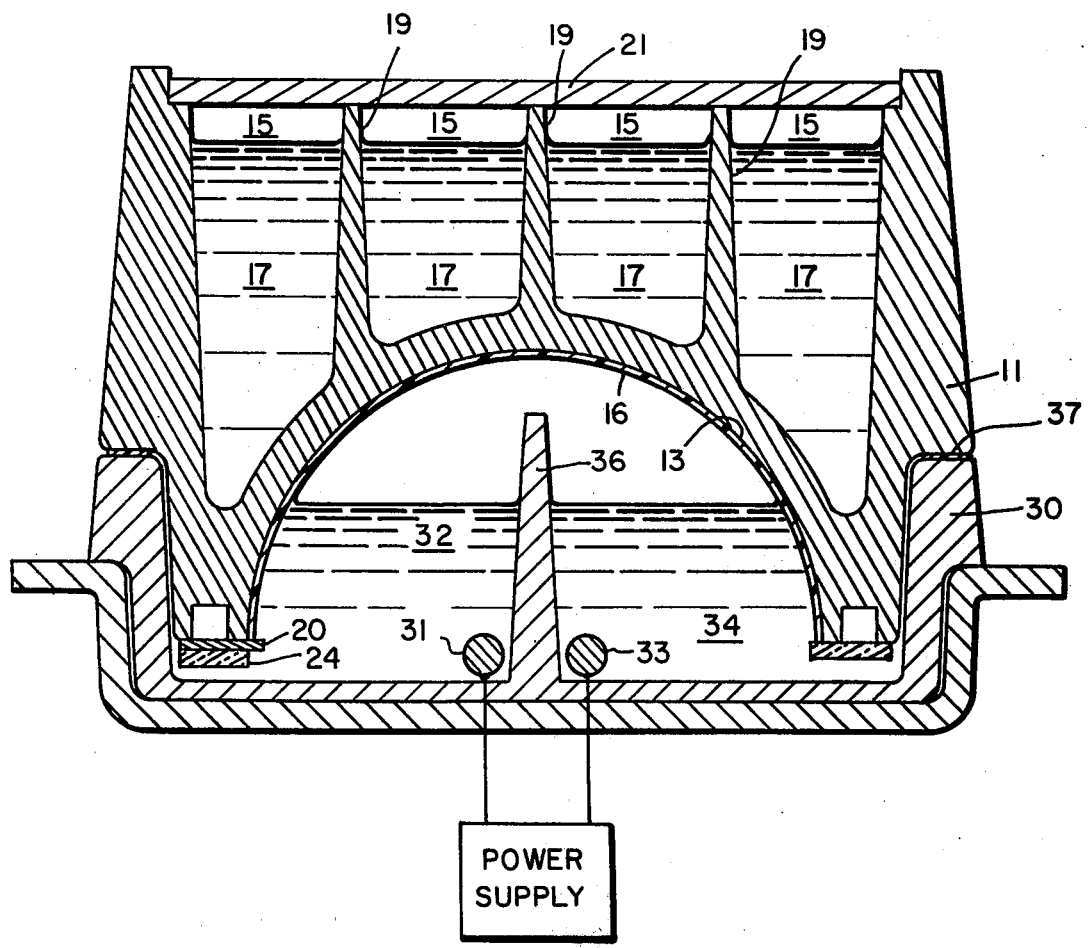

With reference now to FIG. 1, the mounting and cooling block generally indicated at 11 is formed of an aluminum casting and includes a concave cylindrical external surface 13. In the hollow portions 15 of the mounting block 11 a material 17, such as lithium salt, is located. The mounting block may be formed with internal cooling fins 19, and includes a cover 21 which may be sealably attached to the mounting block 11 itself, by means of screws or the like (not shown). The concave surface 13 is preferably coated with an electrically insulating material, which is chemically nonreactive with the buffer solution and which should also be hydrophobic in order to avoid wetting of the cooling block which would result in an uneven temperature distribution across the surface of the electrophoretic slide. A suitable material is a coating of polyphenylene sulfide resin, such as that manufactured under the trademark Ryton by Phillips Petroleum Company of Bartelsville, Okla., U.S.A. An electrophoretic slide 16 is shown mounted in continuous intimate contact with the concave surface 13. The slide is formed of an agarose gel layered on a substrate of polyethylene. Typical dimensions for the slide are 6 inches wide by 9.24 inches in length, with the polyethylene substrate having a thickness of 0.007 inches. In order to provide for ease in handling the agarose gel covers the entire surface of the slide, with the exception of a ¾ inches strip along each of the long sides of the polyethylene substrate. In handling, the slides can then be handled along these ¾ inches strips, without contamination of the agarose gel material.

The material 17 is any suitable material which has a phase change in the desired range and the property of absorption of sufficient heat associated with the phase change to maintain the slide at a constant temperature. We have found that certain salts are particularly useful for this purpose, the phase change being from a solid to a liquid phase. One salt which we have used is hydrated lithium nitrate. The cooling block 11 includes about 800 milliliters of this material, which has a heat of fusion of about 70 calories per gram. This material is also desirable because of its relatively high density, so that a significant amount of the material will occupy a relatively small volume.

To position the slide on the mounting block 11, the slide is moved, with the substrate side uppermost, into position so that one end presses against a compressible lip element 20, which typically could be formed of silicon, or rubber or other soft resilient material, which is inert to the buffer solution. The lip 20 is held in position by a retainer 24, formed of glass filled board or other equivalent material. The opposite end of the slide 16 is then allowed to slip against the retaining element 24 and the resilient lip 20 retains the slide generally in compression against the concave surface 13 to provide for continuous intimate contact. The retaining element 24 may also be formed of glass filled board. Alternative arrangements for retaining the slide include the use of spring retaining elements.

The buffer reservoir 30 which may be formed, for example, of cast epoxy, includes two isolated buffer cells 32 and 34 with a relatively high separator 36 between them. One electrode 31 lies within the buffer cell 32, while an identical electrode 33 lies within the buffer solution cell 34. The upper edge of the reservoir member 30 contains a sealing gasket 37 to avoid spillage of the buffer solution when the mounting block 11 is placed in position on the reservoir 30. In operation a power supply, capable of providing a voltage of approximately 200 volts at a peak amperage of approximately 300 amps. is connected between electrodes 31 and 33. A typical migration time is in the order of 45 minutes to 1 hour.

The buffer solution may be any suitable electrophoresis buffer solution such as a mixture of 0.331 gms of diethyl barbituric acid +1.848 gms of sodium diethyl barbiturate to 120 mils. of distilled water (ph 8.6, ionic strength 0.075).

It has been found that with the material 17 described above, the mounting block may be utilized to process as many as four slides, before it needs to be recycled. The recycling of the mounting block consists in allowing it to stand overnight at room temperature so that the salt may solidify or, if a shorter recycling time is desired, the block may be recycled by placing it for about one hour in an ice bath.

While a specific geometric configuration of the apparatus has been described, and specific materials have been given as examples, it will be understood that other materials may be employed with other configurations and that the invention should be construed as being defined by the associated claims.

I claim:

1. In an electrophoresis migration apparatus having a mounting block with a concave cylindrical external surface for mounting and holding an electrophoresis slide, the improvement comprising;
   a first slide retaining member fastened adjacent one edge of said concave cylindrical surface and extending in a direction substantially normal to said surface, said first retaining member being formed of a resilient soft material;
   a second retaining member formed of a substantially rigid material, said second retaining member being mounted near the opposite edge of said concave cylindrical surface and extending in a direction substantially normal to said concave cylindrical surface toward said first retaining member, whereby an electrophoresis slide may be mounted and maintained compressed against said concave cylindrical surface by the resilient action of said first member compressing said slide lengthwise against said second rigid member.

2. The improvement of claim 1 wherein said first retaining member is formed of closed cell rubber.

3. The improvement of claim 1 wherein said first retaining element is formed of silicone elastomer.

* * * * *